United States Patent
Wahlstrand et al.

(10) Patent No.: US 7,392,089 B2
(45) Date of Patent: *Jun. 24, 2008

(54) REDUCING RELATIVE INTERMODULE MOTION IN A MODULAR IMPLANTABLE MEDICAL DEVICE

(75) Inventors: Carl D. Wahlstrand, Lino Lakes, MN (US); Darren A. Janzig, Centerville, MN (US); Robert M. Skime, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 679 days.

This patent is subject to a terminal disclaimer.

(21) Appl. No.: 10/731,881

(22) Filed: Dec. 9, 2003

(65) Prior Publication Data

US 2004/0176819 A1    Sep. 9, 2004

Related U.S. Application Data

(60) Provisional application No. 60/431,854, filed on Dec. 9, 2002, provisional application No. 60/471,262, filed on May 16, 2003, provisional application No. 60/503,945, filed on Sep. 20, 2003, provisional application No. 60/503,946, filed on Sep. 20, 2003, provisional application No. 60/507,857, filed on Oct. 1, 2003.

(51) Int. Cl.
   *A61N 1/36* (2006.01)
(52) U.S. Cl. .................................... 607/36
(58) Field of Classification Search ............ 607/36, 607/37, 46–48, 56–58, 137; 128/897–899; 623/10; 600/25
See application file for complete search history.

(56) References Cited

U.S. PATENT DOCUMENTS

| | | | |
|---|---|---|---|
| 3,690,325 A | 9/1972 | Kenny | |
| 3,720,874 A | 3/1973 | Gorcik et al. | |
| 3,724,467 A | 4/1973 | Avery et al. | |
| 3,913,587 A | 10/1975 | Newash | |
| 4,010,760 A | 3/1977 | Kraska et al. | |
| 4,013,081 A | 3/1977 | Kolenik | |
| 4,040,412 A | 8/1977 | Sato | |
| 4,256,115 A | 3/1981 | Bilitch | |
| 4,266,552 A | 5/1981 | Dutcher et al. | |

(Continued)

FOREIGN PATENT DOCUMENTS

DE    3940632    12/1990

(Continued)

OTHER PUBLICATIONS

U.S. Appl. No. 10/731,868, filed Dec. 9, 2003, entitled "Implantation of Low-Profile Implantable Medical Device."
U.S. Appl. No. 10/731,699, filed Dec. 9, 2003, entitled "Coupling Module of a Modular Implantable Medical Device."
U.S. Appl. No. 10/730,873, filed Dec. 9, 2003, entitled "Overmold for a Modular Implantable Medical Device."

(Continued)

*Primary Examiner*—Carl H. Layno
*Assistant Examiner*—Jessica Reidel
(74) *Attorney, Agent, or Firm*—Shumaker & Sieffert, P.A.

(57) ABSTRACT

A modular implantable medical device includes a plurality of modules that are at least partially encapsulated by an overmold. The modules may be connected by coupling modules, which may be flexible to provide for one or more degrees of relative intermodular motion. The overmold may also be flexible. In order to reduce relative intermodule motion to acceptable direction and/or ranges, the overmold may include one or more motion reduction elements.

27 Claims, 12 Drawing Sheetse

U.S. PATENT DOCUMENTS

| | | |
|---|---|---|
| 4,328,813 A | 5/1982 | Ray |
| 4,399,819 A | 8/1983 | Cowdery |
| 4,399,820 A | 8/1983 | Wirtzfeld et al. |
| 4,499,907 A | 2/1985 | Kallok et al. |
| 4,616,655 A | 10/1986 | Weinberg et al. |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A * | 11/1990 | Owens et al. ............... 607/129 |
| 5,085,644 A | 2/1992 | Watson et al. |
| 5,197,332 A | 3/1993 | Shennib |
| 5,220,929 A | 6/1993 | Marquit |
| 5,271,397 A | 12/1993 | Seligman et al. |
| 5,314,451 A | 5/1994 | Mulier |
| 5,314,453 A | 5/1994 | Jeutter |
| H1465 H | 7/1995 | Stokes |
| 5,455,999 A | 10/1995 | Weiss et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,613,935 A * | 3/1997 | Jarvik .......................... 600/16 |
| 5,638,832 A | 6/1997 | Singer et al. |
| 5,645,586 A | 7/1997 | Meltzer |
| 5,674,260 A | 10/1997 | Weinberg |
| 5,678,559 A | 10/1997 | Drakulic |
| 5,702,430 A | 12/1997 | Larson, Jr. et al. |
| 5,741,313 A | 4/1998 | Davis et al. |
| 5,755,743 A | 5/1998 | Volz et al. |
| 5,769,874 A | 6/1998 | Dahlberg |
| 5,776,169 A | 7/1998 | Schroeppel |
| 5,800,535 A | 9/1998 | Howard, III |
| 5,814,095 A | 9/1998 | Müller et al. |
| 5,843,150 A | 12/1998 | Dreessen et al. |
| 5,873,899 A * | 2/1999 | Stutz et al. ................... 607/36 |
| 5,895,414 A | 4/1999 | Sanchez-Zambrano |
| 5,896,647 A | 4/1999 | Shkuratoff |
| 5,919,215 A | 7/1999 | Wiklund et al. |
| 5,935,154 A | 8/1999 | Westlund |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,016,593 A | 1/2000 | Kyrstein |
| 6,061,593 A | 5/2000 | Fischell et al. |
| 6,067,474 A | 5/2000 | Schulman et al. |
| 6,091,979 A | 7/2000 | Madsen |
| 6,128,538 A | 10/2000 | Fischell et al. |
| 6,131,581 A | 10/2000 | Leysieffer et al. |
| 6,134,474 A | 10/2000 | Fischell et al. |
| 6,168,580 B1 | 1/2001 | Yardley |
| 6,176,879 B1 | 1/2001 | Reischl et al. |
| 6,214,032 B1 | 4/2001 | Loeb et al. |
| 6,230,049 B1 | 5/2001 | Fischell et al. |
| 6,248,080 B1 | 6/2001 | Miesel et al. |
| 6,259,951 B1 | 7/2001 | Kuzma et al. |
| 6,266,556 B1 | 7/2001 | Ives et al. |
| 6,269,266 B1 | 7/2001 | Leysieffer |
| 6,272,382 B1 | 8/2001 | Faltys et al. |
| 6,308,101 B1 | 10/2001 | Faltys et al. |
| 6,324,428 B1 | 11/2001 | Weinberg et al. |
| 6,330,468 B1 | 12/2001 | Scharf |
| 6,354,299 B1 | 3/2002 | Fischell et al. |
| 6,356,792 B1 | 3/2002 | Errico et al. |
| 6,358,281 B1 | 3/2002 | Berrang et al. |
| 6,360,122 B1 | 3/2002 | Fischell et al. |
| 6,427,086 B1 | 7/2002 | Fischell et al. |
| 6,445,956 B1 | 9/2002 | Laird et al. |
| 6,480,743 B1 | 11/2002 | Kirkpatrick et al. |
| 6,490,486 B1 | 12/2002 | Bradley |
| 6,516,227 B1 | 2/2003 | Meadows et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |
| 6,671,544 B2 | 12/2003 | Baudino |
| 6,726,678 B1 | 4/2004 | Nelson et al. |
| 6,788,974 B2 | 9/2004 | Bardy et al. |
| 6,805,998 B2 | 10/2004 | Jenson et al. |
| 7,103,415 B2 | 9/2006 | Probst et al. |
| 7,212,864 B2 * | 5/2007 | Wahlstrand et al. ........... 607/36 |
| 7,242,982 B2 * | 7/2007 | Singhal et al. ................ 607/36 |
| 7,263,401 B2 * | 8/2007 | Scott et al. .................... 607/36 |
| 2001/0033953 A1 | 10/2001 | Gan et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0051550 A1 | 5/2002 | Leysieffer |
| 2002/0068958 A1 | 6/2002 | Bardy et al. |
| 2002/0087201 A1 | 7/2002 | Firlik et al. |
| 2002/0099412 A1 | 7/2002 | Fischell et al. |
| 2002/0103510 A1 | 8/2002 | Bardy et al. |
| 2002/0165588 A1 | 11/2002 | Fraley et al. |
| 2003/0004428 A1 | 1/2003 | Pless et al. |
| 2003/0004546 A1 | 1/2003 | Casey |
| 2003/0040781 A1 | 2/2003 | Larson et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0109903 A1 | 6/2003 | Berrang et al. |
| 2003/0120513 A1 * | 6/2003 | Solom ........................ 607/36 |
| 2003/0130706 A1 | 7/2003 | Sheffield et al. |
| 2003/0171787 A1 | 9/2003 | Money et al. |
| 2004/0082977 A1 | 4/2004 | Engmark et al. |
| 2004/0176815 A1 | 9/2004 | Janzig et al. |

FOREIGN PATENT DOCUMENTS

| | | |
|---|---|---|
| GB | 1 161 579 | 8/1969 |
| WO | WO 92/20402 | 11/1992 |
| WO | WO 00/13743 | 3/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/97906 | 12/2001 |
| WO | WO 02/05590 | 1/2002 |
| WO | WO 02/056637 | 7/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |
| WO | WO 2004/052458 | 6/2004 |

OTHER PUBLICATIONS

U.S. Appl. No. 10/730,878, filed Dec. 9, 2003, entitled "Lead Interconnect Module of a Modular Implantable Medical Device."
U.S. Appl. No. 10/730,877, filed Dec. 9, 2003, entitled "Low-Profile Implantable Medical Device."

U.S. Appl. No. 10/731,867, filed Dec. 9, 2003, entitled "Concavity of an Implantable Medical Device."
U.S. Appl. No. 10/731,638, filed Dec. 9, 2003, entitled "Modular Implantable Medical Device."
U.S. Appl. No. 10/731,869, filed Dec. 9, 2003, entitled "Modular Implantable Medical Device."
"Surgical Process," Animation Screenshots from http://www.cochlearamerica.com/800.asp, 7 pgs.
"Candidates Brochure," http://www.cochlearamerica.com/pdfs/candidatebrochglobal.pdf, 14 pgs.
"Research and Development," http://www.cochlearamericas.com/384.asp, 1 pg.
"The World Leader in cochlear implants—revolutionizing hearing for adults and infants," http://www.cochlear.com, 1 pg.
"Cochlear: innovator of the Nucleus 3 cochlear implant system," http://www.cochlearamericas.com, 1 pg.
"What is a Cochlear Implant," http://www.cochlearamericas.com/What/161.asp, 1 pg.
"ESPrit 3G Speech Processor," http://www.cochlearamericas.com/591.asp, 2 pgs.
"Nucleus 3 System," http://www.cochlearamericas.com/Products/465.asp, 1 pg.
"Internal Components: Nucleus 24 Cochlear Implants," http://www.cochlearamericas.com/374.asp, 1 pg.
"Nucleus 24 Contour," http://www.cochlearamericas.com/568.asp, 2 pgs.
"Nucleus 24 M," http://www.cochlearamericas.com/372.asp, 1 pg.
"Nucleus 24 K," http://www.cochlearamericas.com/371.asp, 1 pg.
"Nucleus 24 Double Array," http://www.cochlearamericas.com/370.asp, 1 pg.
"Nucleus 24 ABI: Auditory Brainstem Implant," http://www.cochlearamericas.com/373.asp, 2 pgs.
"Nucleus Speech Processors," http://www.cochlearamericas.com/629.asp, 1 pg.
"Sprint: body worn speech processor," http://www.cochlearamericas.com/1010.asp, 1 pg.
"Cochlear," http://www.cochlearamericas.com/Recipients/978.asp, 3 pgs.
Notification of Transmittal of the International Search Report dated May 7, 2004, International Application No. PCT/US03/38926.
Written Opinion dated Dec. 16, 2004, International Application No. PCT/US03/38926.
Notification of Transmittal of the International Preliminary Examination Report dated Apr. 11, 2005, International Application No. PCT/US03/38926.
U.S. Appl. No. 10/837,319, filed Apr. 30, 2004, entitled "Implantable Medical Device With Anti-Infection Agent."
U.S. Appl. No. 10/835,527, filed Apr. 29, 2004, entitled "Implantation of Implantable Medical Device".
U.S. Appl. No. 10/835,232, filed Apr. 29, 2004, entitled "Explanation of Implantable Medical Device."
U.S. Appl. No. 10/835,233, filed Apr. 29, 2004, entitled "Implantable Medical Device With A Nonhermetic Battery."
U.S. Appl. No. 10/835,548, filed Apr. 29, 2004, entitled "Headset Recharger For Cranially Implantable Medical Devices."
U.S. Appl. No. 10/835,245, filed Apr. 29, 2004, entitled "Battery Housing Configuration."
U.S. Appl. No. 10/837,276, filed Apr. 30, 2004, entitled "Implantable Medical Device With Lubricious Material."
Answers.com, www.answers.com, defined: discrete components, acessed on Mar. 2, 2007 (2 pages).

* cited by examiner

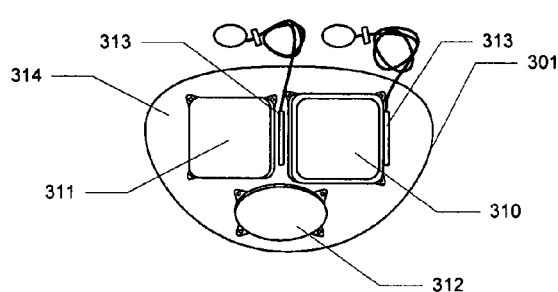
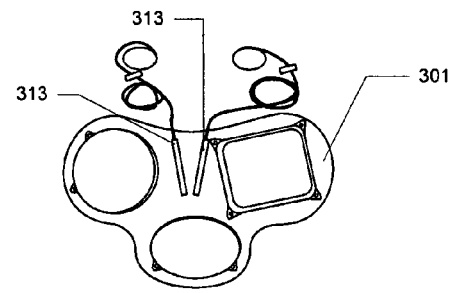
FIG. 3A  FIG. 3B
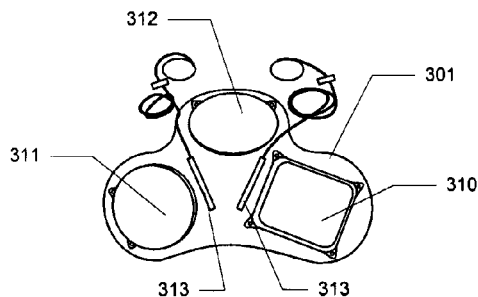
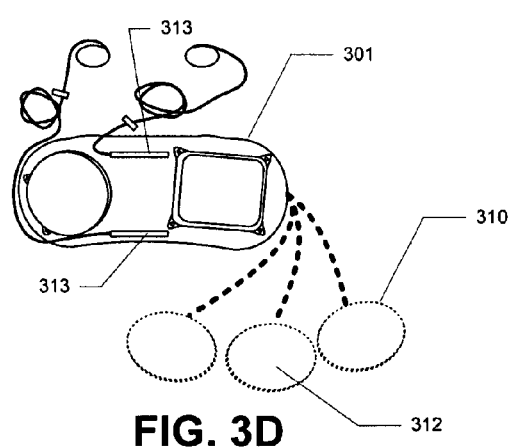
FIG. 3C  FIG. 3D
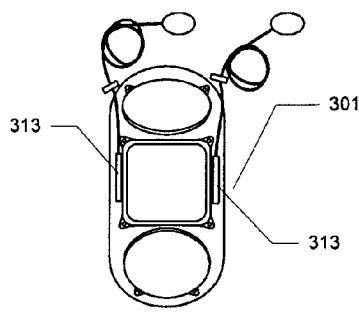
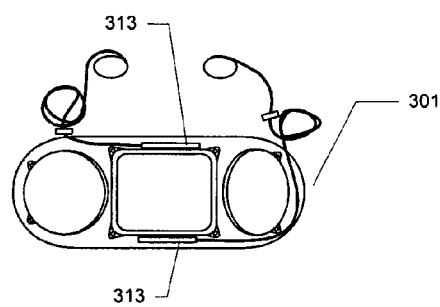
FIG. 3E  FIG. 3F

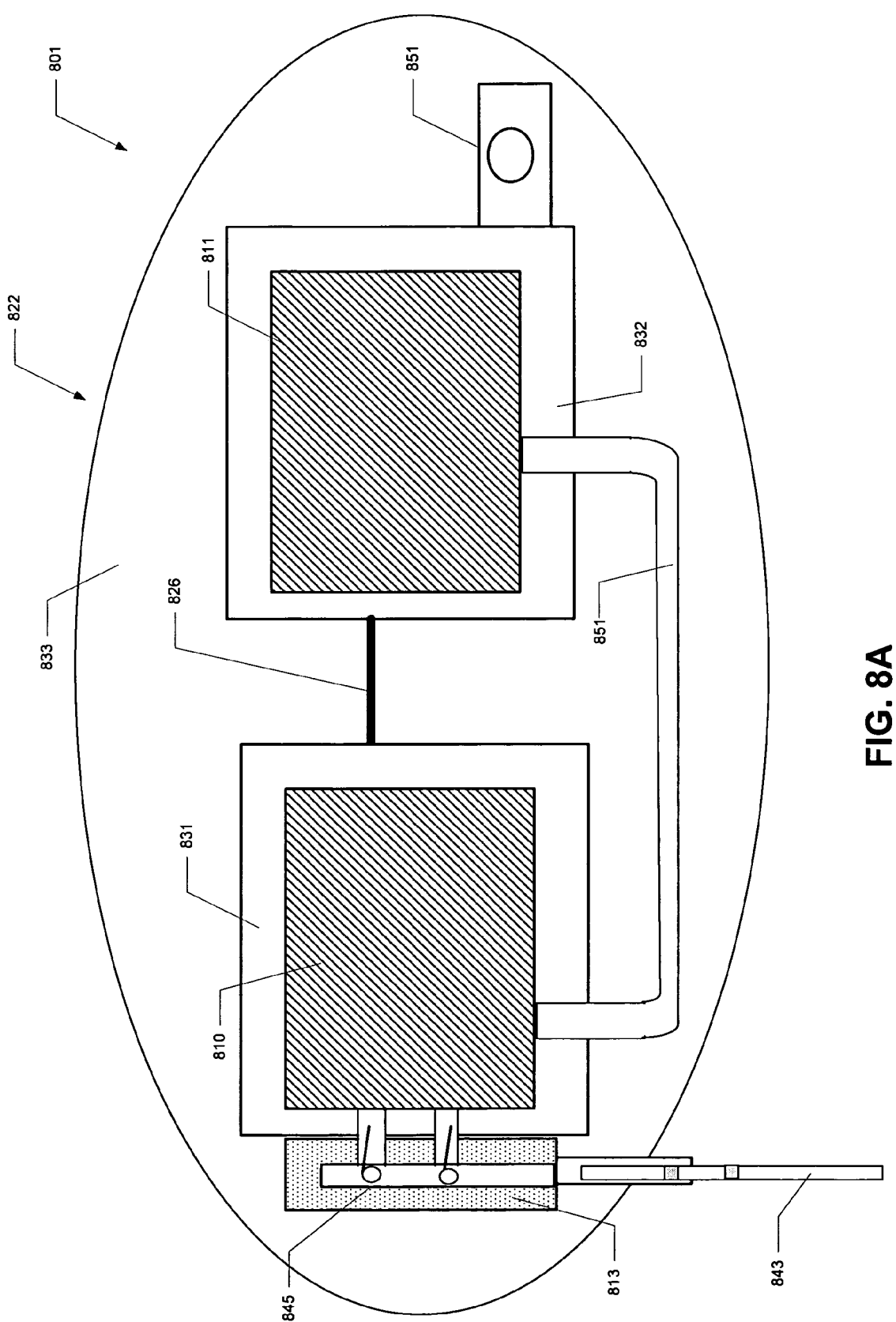

REDUCING RELATIVE INTERMODULE MOTION IN A MODULAR IMPLANTABLE MEDICAL DEVICE

This application claims the benefit of:
1. U.S. Provisional Application entitled "CRANIAL NEUROSTIMULATOR AND METHOD," Serial No. 06/431,854, filed on Dec. 9, 2002;
2. U.S. Provisional Application entitled "IMPLANTABLE CRANIAL MEDICAL DEVICES AND METHODS," Serial No. 60/471,262, filed on May 16, 2003;
3. U.S. Provisional Application entitled "IMPLANTABLE CRANIAL MEDICAL DEVICES AND METHODS," Serial No. 60/503,945, filed on Sep. 20, 2003;
4. U.S. Provisional Application entitled "IMPLANTABLE CRANIAL MEDICAL DEVICES AND METHODS," Serial No. 60/503,946, filed on Sep. 20, 2003; and
5. U.S. Provisional Application entitled "THIN NEURO STIMULATION SYSTEM, DEVICE AND METHOD," Serial No. 60/507,857, filed on Oct. 1, 2003. The entire content of each of these U.S. Provisional Applications is incorporated herein by reference.

The following co-pending and commonly-assigned U.S. Patent Applications, filed on even date herewith, are also incorporated herein by reference:
1. U.S. patent application entitled "MODULAR IMPLANTABLE MEDICAL DEVICE," to Wahlstrand et al, Ser. No. 10/731,869, filed Dec. 9, 2003;
2. U.S. patent application entitled "IMPLANTATION OF LOW-PROFILE IMPLANTABLE MEDICAL DEVICE," to Singhal et al., Ser. No. 10/731,868, filed Dec. 9, 2003;
3. U.S. patent application entitled "OVERMOLD FOR A MODULAR IMPLANTABLE MEDICAL DEVICE," to Singhal et al., Ser. No. 10/730,873, filed Dec. 9, 2003;
4. U.S. patent application entitled "COUPLING MODULE FOR A MODULAR IMPLANTABLE MEDICAL DEVICE," to Janzig et at, Ser. No. 10/731,699, filed Dec. 9, 2003;
5. U.S. patent application entitled "LEAD INTERCONNECT MODULE OF A MODULAR IMPLANTABLE MEDICAL DEVICE," to Singhal et al., Ser. No. 10/730,878, filed Dec. 9, 2003;
6. U.S. patent application entitled "LOW PROFILE IMPLANTABLE MEDICAL DEVICE," to Janzig et al., No. 10/730,877, filed Dec. 9, 2003;
7. U.S. patent application Ser. No. entitled "CONCAVITY OF A IMPLANTABLE MEDICAL DEVICE AND MODULES THEREOF," to Wahlstrand et al., Ser. No. 10/731,867, filed Dec. 9, 2003; and
8. U.S. patent application Ser. No. entitled "MODULAR IMPLANTABLE MEDICAL DEVICE," to Wahlstrand et al., Ser. No. 10/731,638, filed Dec. 9, 2003.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a hybrid circuit that includes digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention relates to techniques for reducing relative intermodular motion within a modular implantable medical device. Various functional components of a modular implantable medical device are separated into interconnected modules. This distributed architecture for the implantable medical device may permit the device footprint to be distributed over a larger area while making the profile smaller. In addition, the multiple modules and the flexible interconnections between the modules may permit the overall shape of the implantable medical device to be formed to better match the body location into which it is to be implanted.

An overmold integrates the modules of a modular implantable medical device into a structure. In exemplary embodiments, the overmold is flexible, e.g., allows intermodule motion, and provides a biocompatible interface between the component modules and the patient. Further, the modules may be coupled to each other by coupling modules, which may include a lumen to carry a conductor or a fluid. A coupling module may be hermetic, may be flexible to allow at least one degree of relative motion between the modules that it couples. The coupling module may be shaped and/or constructed to provide such flexibility.

However, too much intermodular motion can compromise the structural integrity of the coupling module, which may lead to failure of a modular implantable medical device. Consequently, the overmold includes as least one motion reduction element to reduce relative motion between modules of a modular implantable medical device. The motion reduction element may couple modules, and may include, for example a wire-like element of a cloth element. In some embodiments, components of the overmold provide motion restriction elements that interact to reduce relative motion between modules with which the components are associated.

In some embodiments, a motion reduction element includes a mechanical locking mechanism. In such embodiments, the modules of a modular implantable medical device can be manipulated into a configuration and locked into that configuration. The mechanical locking mechanism can, for example, include an element to receive a pin inserted within the overmold to lock the motion reduction element.

In one embodiment, the invention is directed to an implantable medical device that includes a plurality of interconnected modules and an overmold. Each of the modules includes a housing, and the overmold at least partially encapsulates each of the housings. The implantable medical device further includes a motion reduction element within the overmold to reduce the relative motion between at least two of the modules.

In another embodiment, the invention is directed to an implantable medical device that includes a plurality of interconnected modules and an overmold. Each of the modules includes a housing, and the overmold at least partially encapsulates each of the housings. The implantable medical device further includes means within the overmold for reducing relative intermodular motion between at least two of the modules.

In another embodiment, the invention is directed to an implantable medical device that includes a plurality of interconnected modules and an overmold. Each of the modules includes a housing, and the overmold at least partially encapsulates each of the housings. The implantable medical device further comprises and coupling module, and a motion reduction element within the overmold. The coupling module couples at least two of the modules, and is flexible to allow at least one degree of motion between the modules. The motion reduction element reduces relative intermodule motion between the at least two of the modules in the at least one degree.

In another embodiment, the invention is directed to a method that includes manipulating a modular implantable medical device into a configuration, and locking the implantable medical device within the configuration.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A-3F are schematic diagrams illustrating various arrangements of modules within a modular implantable medical device according to various embodiments of the present invention.

FIG. 8A-8B are a schematic diagrams illustrating multiple modules of a modular implantable medical device connected by a motion reduction element according to the present invention.

DETAILED DESCRIPTION

Figure 1A:
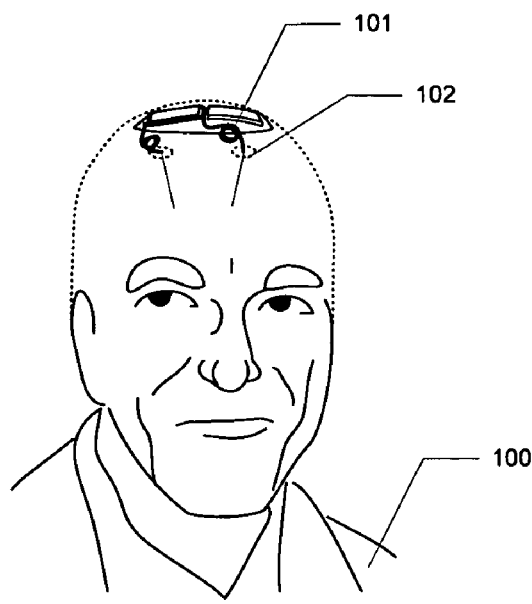
FIGS. 1A and 1B are diagrams illustrating a modular implantable medical device implanted in a patient according to an example embodiment of the present invention.
Figure 1B:
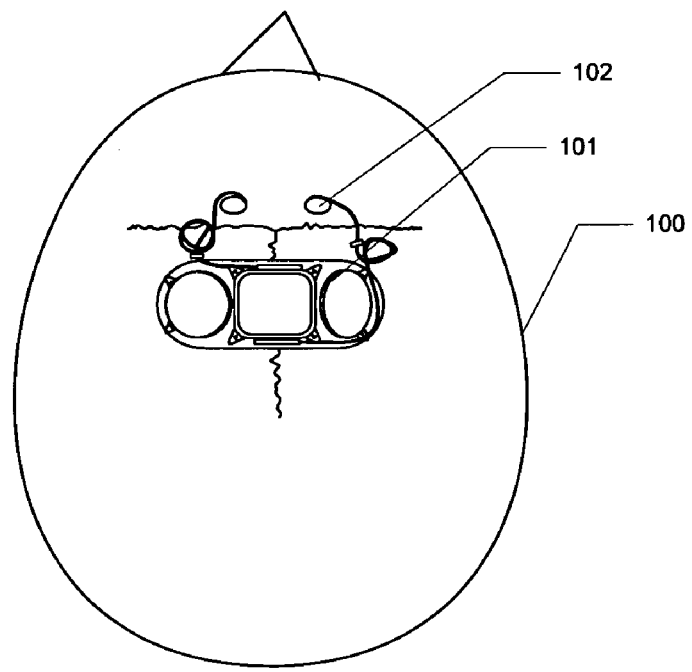

FIGS. 1A and 1B are diagrams illustrating a modular implantable medical device 101 implanted within a patient 100. By constructing modular implantable medical device 101 as a set of distributed modules connected together as described herein, modular implantable medical device 101 may be implanted at locations for which implantation of conventional implantable medical devices has been deemed undesirable, thus permitting the implantable medical device 101 to be implanted near a monitoring and/or therapy delivery location. In the example illustrated within FIGS. 1A-1B, modular implantable medical device 101 is implanted under the scalp of the patient 100 in order to locate the device 101 close to the location to which therapy is to be delivered via leads 102, i.e., the brain of patient 100. The low profile and the shape of modular implantable medical device 101 as described herein can reduce the risk of infection and skin erosion associated with implantation of matter beneath the scalp, and may provide a cosmetically acceptable profile when implanted beneath the scalp.

Modular implantable medical device 101 may deliver stimulation to the brain of patient 100 to, for example, provide deep brain stimulation (DBS) therapy, or to stimulate the cortex of the brain. Cortical stimulation may involve stimulation of the motor cortex. Modular IMD 101 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular implantable medical device 101 is not limited to delivery of stimulation to the brain of patient 100, and may be employed with leads 102 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular implantable medical device 101 is not limited to implantation under the scalp of patient 100. Indeed, modular implantable medical device 101 may be implanted anywhere within patient 100. For example, modular implantable medical device 101 can be implanted within the neck of patient 100, and deliver stimulation to the vagus nerve or the cervical region of the spinal cord.

Modular implantable medical device 101 may alternatively be implanted within a pectoral region or the abdomen of patient 100 to act as a diaphragmatic pacer, or to provide any of the monitoring and therapy delivery functions known in the art to be associated with cardiac pacemakers. Further, modular implantable medical device 101 may be implanted in the upper buttock region and deliver spinal cord, urological or gastrological stimulation therapy, or may be configured to be implanted within the periphery, e.g., limbs, of patient 100 for delivery of stimulation to the muscles and/or peripheral nervous system of patient 100. As is the case with cranial implantation, the modularity of implantable medical device 101 may enable implantation at some of these example locations for which implantation of conventional implantable medical devices is generally deemed undesirable.

Modular implantable medical device 101 is not limited to embodiments that deliver stimulation. For example, in some embodiments modular implantable medical device 101 may additionally or alternatively monitor one or more physiological parameters and/or the activity of patient 100, and may include sensors for these purposes. Where a therapy is delivered, modular implantable medical device 101 may operate in an open loop mode (also referred to as non-responsive operation), or in a closed loop mode (also referred to as responsive). Modular implantable medical device 101 may also provide warnings based on the monitoring.

As discussed above, the ability of a modular implantable medical device 101 according to the invention to be implanted close to a region within patient 100 to be monitored enables the use of shorter leads 102. Shorter leads 102 may advantageously improve the accuracy of such sensors by reducing noise attributable to leads 102. Shorter leads 102 may also advantageously reduce the negative affects of imaging techniques such as magnetic resonance imaging "MRI" on a person implanted with implantable medical device 101.

Additional alternate embodiments for implantable medical devices implemented according to principles of the present invention may also include non-electrical based therapies such as targeted introduction of fluids and similar therapeutic materials using pumps and reservoirs of material. One skilled in the art will recognize that any number of implantable devices may be possible without deviating from the spirit and scope of the present invention as recited within the attached claims.

Figure 2:
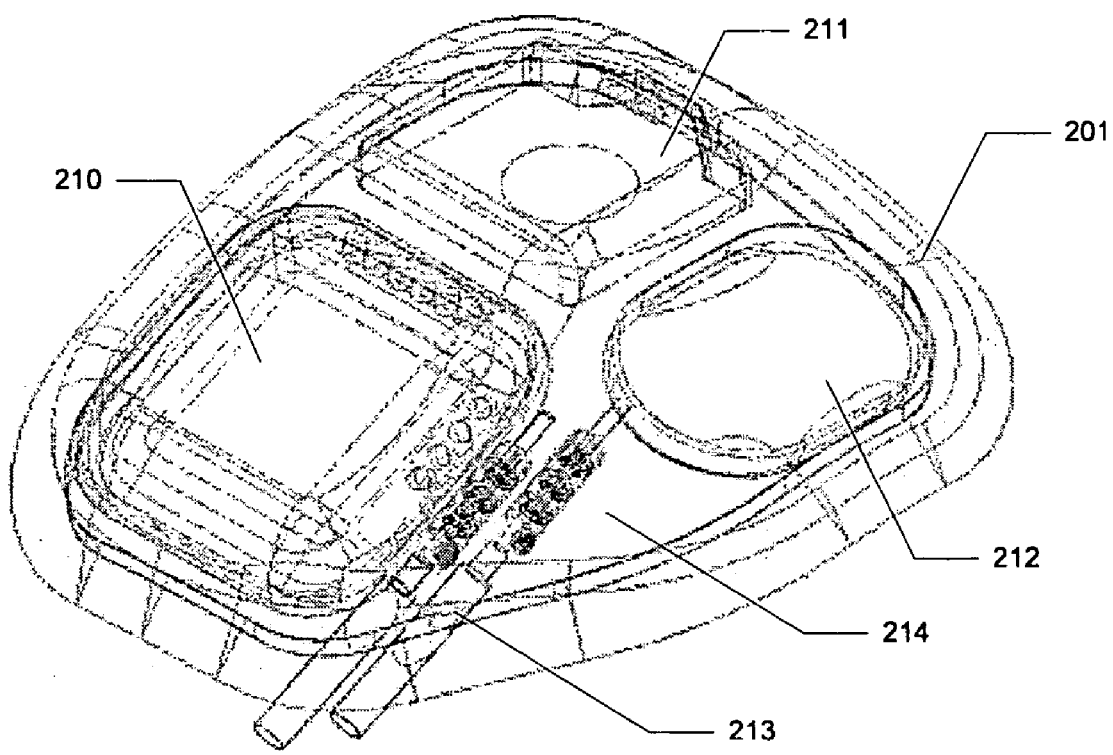
FIG. 2 is a schematic diagram illustrating a modular implantable medical device according to another embodiment of the present invention.

FIG. 2 is a schematic diagram illustrating a modular implantable medical device 201 according to another embodiment of the present invention. In this example embodiment, implantable medical device 201 is arranged in a triangular configuration. Modular implantable medical device 201 includes three modules: a control module 210, a power source module 211, and a recharge module 212. Each of modules 210-212 includes a respective housing. Modular implantable medical device 201 also contains a set of lead connection modules 213 that permits external leads 102 (FIGS. 1A and 1B) to be connected to control module 210 as needed. The distribution of functional components of modular implantable medical device 201 into modules permits modular implantable medical device 201 to possess a thin profile by spreading the components over a larger surface area.

Control module 210 includes control electronics for controlling the monitoring and/or therapy delivery functions of modular implantable medical device 201, such as a microprocessor, and may include therapy delivery circuitry. A housing of control module 210 may be hermetic in order to protect the control electronics therein, and in embodiments is formed of a rigid material, such as titanium, stainless steel, or a ceramic. Power source module 211 includes a power source that provides energy to control module 210, which in some embodiments is a rechargeable power source such as a rechargeable battery and/or capacitor. Recharge module 212 includes a recharge coil for inductively receiving energy to recharge a rechargeable power source within power source module 211. Additional details regarding modules 210, 211 and 212, additional or alternative modules for a modular implantable medical device, may be found in commonly assigned U.S. Patent Application entitled "MODULAR IMPLANTABLE MEDICAL DEVICE," commonly assigned U.S. Patent Application entitled "COUPLING MODULES OP A DISTRIBUTED MODULAR IMPLANTABLE MEDICAL DEVICE," and commonly assigned U.S. Patent Application entitled "LEAD INTERCONNECT MODULE OF A MODULAR IMPLANTABLE MEDICAL DEVICE,"

As illustrated in FIG. 2, modular implantable medical device 201 includes an overmold 214. Overmold 214 at least partially encapsulates modules 210-212. Further, as will be described in greater detail below, lead connection modules 213 may be formed in overmold 214. Overmold integrates modules 210-212 into a structure. Overmold 214 may provide a flexible structure that permits the device 201 to conform to a variety of implant locations. Use of the term "overmold" herein is not intend to limit the invention to embodiments in which overmold 214 is a molded structure. Overmold 214 may be a molded structure, or may be a structure formed by any process.

In some embodiments, overmold 214 may be curved to match the shape of the location within a patient in which the device is being implanted. For example, implantation of modular implantable medical device 201 under the scalp of a patient may be accomplished if overmold 214 is concave to substantially conform to the shape of the cranium of the patient. Concavity of modular implantable medical devices is described in greater detail in a commonly-assigned U.S. patent application Ser. No. 10/731,867, entitled "CONCAVITY OF AN IMPLANTABLE MEDICAL DEVICE." Any number of shapes may be used to match a particular implantable medical device 201 to an implantation location for a device.

Overmold 214 may comprise a solid biocompatible elastomeric material that is soft and flexible such as silicone. In some embodiments, overmold 214 comprises two or more materials, and two or more components. For example, overmold may comprise one or more elastomeric components formed of an elastomeric material, such as silicone, and one or more non-elastomeric components formed of a non-elastomeric material, such as polysulfone, or a polyurethane such as Tecothane®, which is commercially available from Hermedics Polymer Products, Wilmington, Mass. The one or more elastomeric components may provide the overall shape and flexibility of modular implantable medical device 201, while the non-elastomeric components may provide structural integrity for modular implantable medical device 201, integrate the modules within the non-elastomeric, and form a part of the lead interconnection modules 213.

In some embodiments, one or modules may be coupled by coupling modules (not shown). A coupling module may be flexible, and may include a lumen to carry a conductor or a fluid between modules of a modular implantable medical device. In some embodiments, a coupling module is made of a flexible material such as silicone or a flexible polymer. In other embodiments a coupling module is hermetic and made of a substantially less flexible material, such as titanium or stainless steel, and the flexibility of a coupling module is provided by the configuration and/or construction the coupling module.

A coupling module may be flexible in a plurality of directions to provide modules of a modular implantable medical device with multiple degrees of freedom of motion with respect to each other. In exemplary embodiments, a coupling module provides at least three degrees of motion, and the degrees of motion provided include rotational motion. Further details regarding the configuration and/or construction of a coupling module to provide such flexibility may be found below, and within a commonly assigned U.S. patent application Ser. No. 10/731,699, entitled "COUPLING MODULES FOR A MODULAR IMPLANTABLE MEDICAL DEVICE."

Although the overmold and coupling modules are flexible to allow intermodule motion, excessive intermodule motion can compromise the structural integrity of the coupling modules, which could lead to failure of the modular implantable medical device. Consequently, in some embodiments overmold 214 includes one or more motion reduction elements. Motion reduction elements may reduce relative intermodule motion to certain directions and/or degrees. Motion reduction elements are described in greater detail below.

FIGS. 3A-3F are schematic diagrams illustrating various arrangements of multiple modules within a modular implantable medical device 301 according to various embodiments of the present invention. In each of these embodiments, modular implantable medical device 301 has three modules as discussed above in reference to FIG. 2: a control module 310, a power source module 311, and a recharge module 312. These modules may be arranged into a variety of configurations, including those illustrated, as long as any required interconnections needed between the modules may be routed within the device. The various embodiments include triangular configurations, in such as those shown in FIGS. 3A-3C, and inline configurations, such as those shown in FIGS. 3D-3F. The set of lead connection devices 313 may be located in various locations within the device as well.

In some embodiments, such as those illustrated in FIGS. 3A-3C and 3E-3F, an overmold 314 at least partially encapsulates each of modules 310, 311 and 312. In other embodiments, such as that illustrated in FIG. 3D, at least one of the modules 310 of modular IMD 301 is located outside of overmold 314. Module 312 located outside of overmold 314 may, as shown in FIG. 3D, be tethered to overmold 314, allowing module 312 to be freely positioned some significant distance from overmold 314. Additional details relating to configurations of modules within a modular implantable medical devices and tethering of modules of an implantable medical device may be found in a U.S. patent application Ser. No. 10/731,869, entitled "MODULAR IMPLANTABLE MEDICAL DEVICE."

Figure 4A:
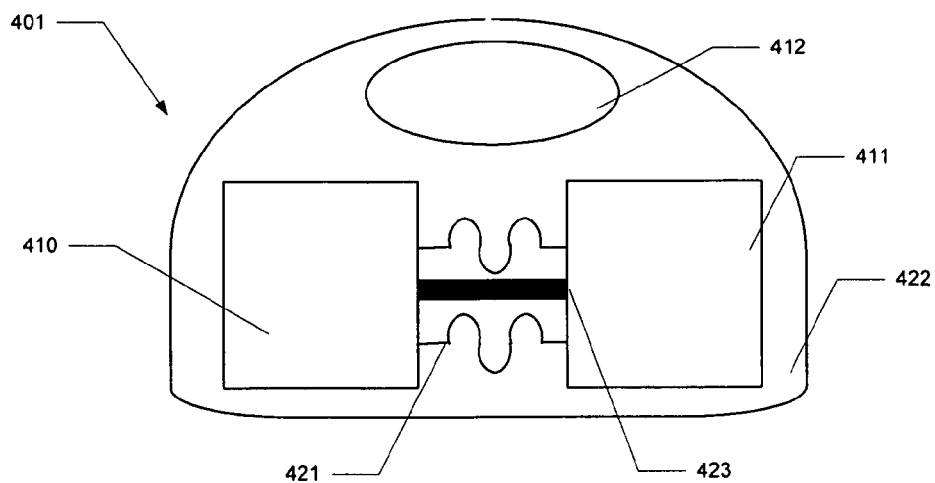
FIGS. 4A-4C are schematic diagrams illustrating the construction of an overmold of a modular implantable medical device according to the present invention.
Figure 4B:
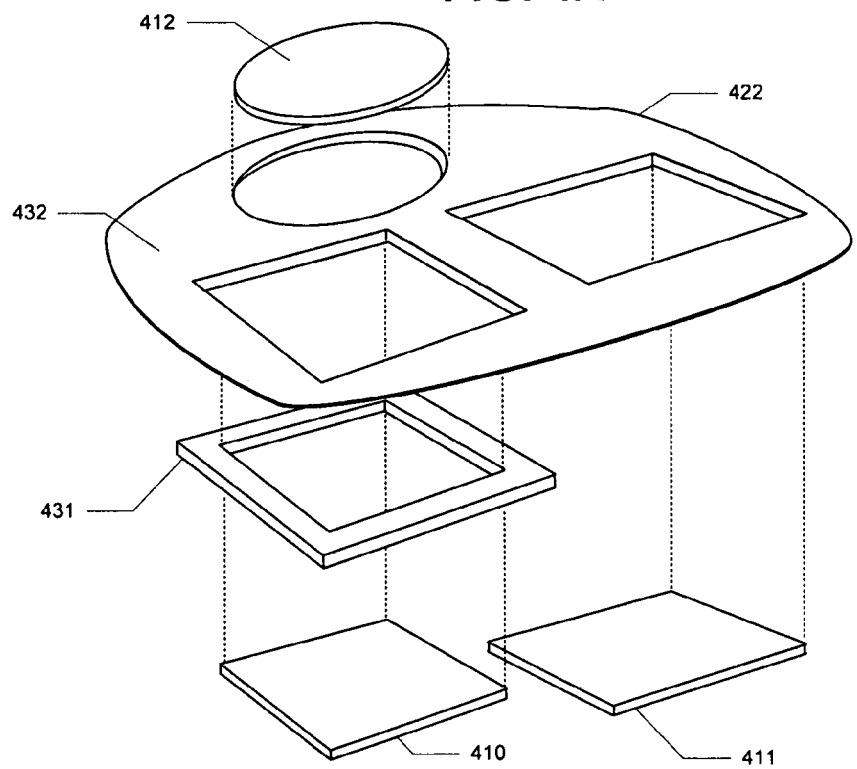
Figure 4C:
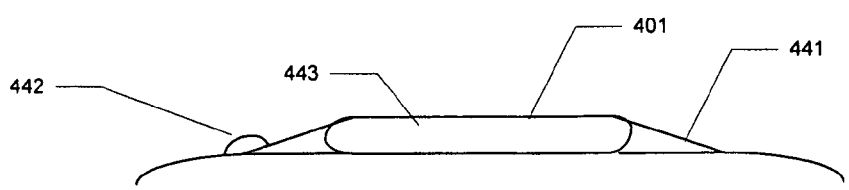

FIGS. 4A-4C are schematic diagrams illustrating an overmold 422 of a modular implantable medical device 401. FIG. 4A illustrates that the modular implantable medical device 401 comprises a set of modules 410-412, a coupling module 423, and a set of motion reduction elements 421 within overmold 422. Because overmold 422 is flexible, overmold 422 may not provide sufficient motion restriction for the modules 410-412. As such, the set of motion restriction elements 421 are used to provide sufficient structural integrity to the device 401 once implanted into the patient 100.

Coupling module 423 provides an interconnection mechanism between components within the set of modules 410-411. This coupling module 423 is typically flexible to permit sufficient motion during implantation and use of the device 401 to minimize mechanical stresses upon the interconnections within the coupling module 423. As such, coupling module 423 alone does not provide sufficient intermodule motion restriction needed by the device 401. The set of motion restriction elements 421 that are separately coupled between the set of modules 410-411 may provide the needed structural support and reduction of intermodule motion.

In the embodiment illustrated within FIG. 4A, the set of motion restriction elements 421 comprises a pair of elements having a plurality of non-linear bends along the length of the elements 421. These non-linear bends are intended to provide restriction of motion in multiple axes of motion. These elements 421 may be wire-like structures formed of a material such as metal. Alternatively, these elements may be constructed of fabric, fibers, and similar rigid and semi-rigid materials. The choice of a material may control the amount of motion restriction any particular motion reduction element 421 may provide. The motion reduction elements 421 need only provide sufficient motion restriction to prevent mechanical fatigue and failure of the coupling module 423. Because the: coupling module 423 may constructed of various materials and thus require differing amounts of motion restriction, the choice of the material for the motion reduction elements 421 and coupling module 423 are interdependent.

FIG. 4B illustrates that the overmold 422 may include two or more components, which may be made of two or more materials. In particular, FIG. 4B illustrates the overmold 422 includes an elastomeric component 432 and a non-elastomeric component 431. The non-elastomeric component 431 is typically shaped to surround at least one of modules 410-412.

In some embodiments, a plurality of individual non-elastomeric components 431 surround respective modules 410-412. In other embodiments, a non-elastomeric component 431 surrounds a plurality of modules 410-412 to integrate the surrounded modules in a common, semi-rigid structure. In such embodiments, the non-elastomeric component may be referred to as an integration component.

The one or more non-elastomeric components 431 may be used to restrict intermodule motion. Elastomeric component 432 may, as shown in FIG. 4B, at least partially encapsulate each of modules 410-412 and non-elastomeric components 431 to provide a desired form factor for a modular implantable medical device. In some embodiments, non-elastomeric elements 431 are fitted into an elastomeric component 432 to form the overmold 422 before the electronic modules 410-412 are inserted into the device 401.

Generally, overmold 422 provides a number of functions in including attaching to modules and other elements to provide a smooth interface surface for the device as it interacts with the patient and protecting electrical connections and feed thru wires needed to connect modules to external leads.

Overmold 422 may be constructed from a durometric specific material to provide a clinically desirable device. In addition, a material used to construct the overmold 422 may possess a thermal conductivity characteristic to either act as a heat sink if needed to dissipate heat from modules 410-412, or a material to act as an insulator to shield the patient 100 from any excess heat from modules 410-412. Because the implantable medical device 401 may be constructed from a large number of modules to perform a desired task, the materials selected for used in constructing the overmold 422 may vary as needed by each embodiment.

FIG. 4C illustrates that the overmold 422 provides sloped interface 441 between the modules within the device 401 and the patient's body components. In embodiments in which the device 401 is implanted within tight spaces, such as under the scalp, the sloped interface 441 provides a smooth transition between the body and the device modules 410-412. Protrusions are known to cause possible points of stress for tissue that is located over implanted devices, which can, for example, lead to skin erosion in the case of a device implanted under the scalp. As such, the sloped interface 441 attempts to minimize the transition from the modules 410-412 and the edge of the device 401 to eliminate these points of stress. An angle of interface 442 from the patient's body and the sloped interface 441 is greater than 90 degrees. Angle 442 may be between 120 and 150 degrees, is preferably between 130 and 140 degrees, and is most preferably approximately 135 degrees.

Figure 5:
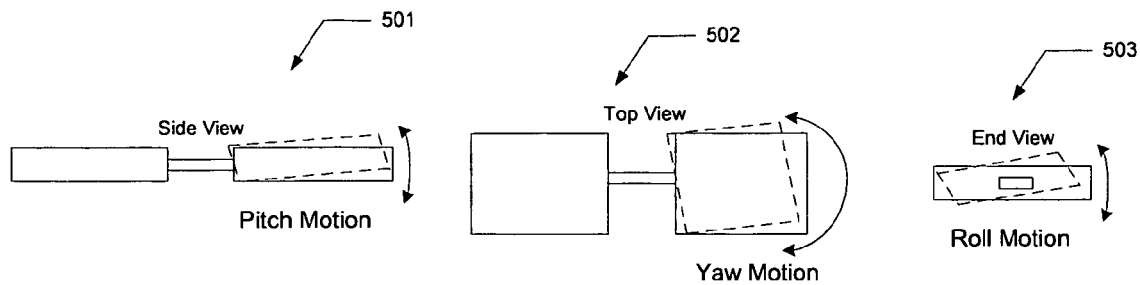
FIG. 5 is a schematic diagram illustrating the degrees of motion present in a modular implantable medical device.

FIG. 5 is a schematic diagram illustrating the degrees of motion present in a multi-module implantable medical device. For any two modules within a modular medical device, motion between the two devices may be defined in terms of pitch motion 501, yaw motion 502, and roll motion 503. For the set of motion reduction elements (not shown) discussed above, all three degrees of motion may be limited to prevent mechanical failures of interconnections between the modules during use of an implantable medical device.

Figure 6A:
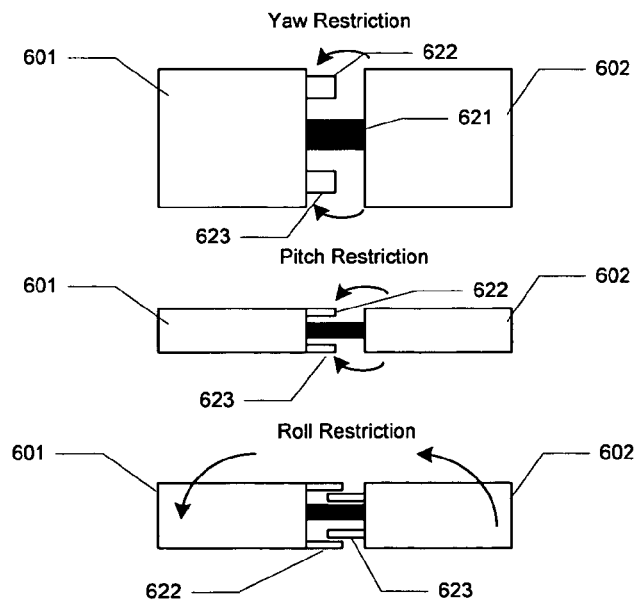
FIGS. 6A-6C are a schematic diagrams illustrating motion reduction within various degrees of motion within a modular implantable medical device.
Figure 6B:
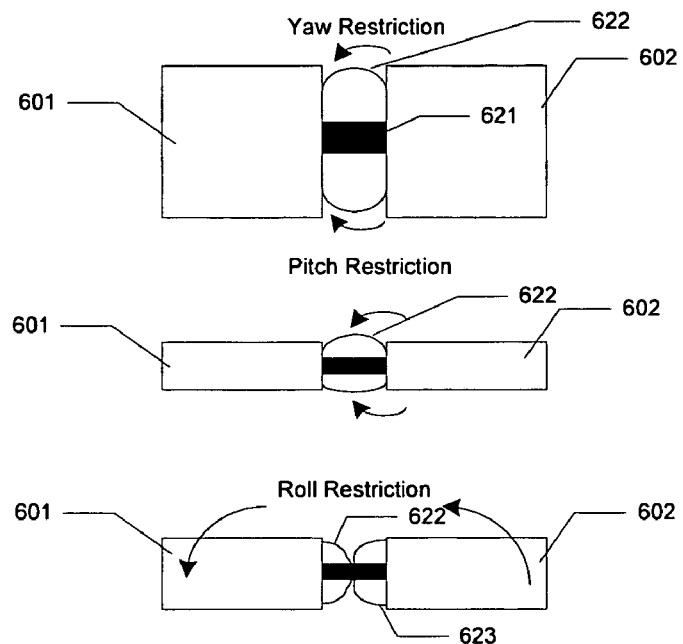
Figure 6C:
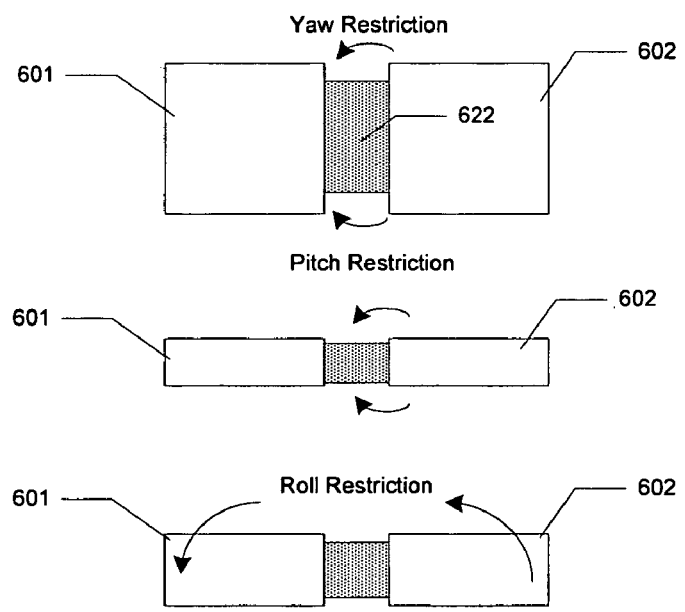

FIGS. 6A-6C are a schematic diagrams illustrating motion reduction within various degrees of motion within a multi-module implantable medical device. For any two modules 601-602 within a modular implantable medical device, one or more motion reduction elements 622-623 may be needed between the modules 601-602. A single motion reduction element 622 may be sufficient to restrain the motion. However, the motion reduction element 622-623 is typically successful in adequately reducing motion in one or two degrees of motion. These degrees of motion are typically along an axis in which the element 622-623 possess its most strength. In the embodiment in FIG. 6A, the motion reduction element 622-623 may restrain the motion between the modules 601-602 along a yaw and pitch axis as the element 622-623 is longer in these axes than in the roll axis. Additional motion reduction elements 622-623 may be required to prevent motion in this third axis.

In some embodiments, motion reduction elements 622-623 are attached a non-elastomeric member 431. In other embodiments, motion reduction elements 622-623 are portions of non-elastomeric member 431 that protrude from the non-elastomeric member 431. In one example illustrated in FIG. 6A motion reduction elements 622-623 comprise physical members associated with respective modules 601 and 602 that physically interact to reduce motion between the modules.

FIG. 6B illustrates an embodiment in which the motion reduction elements 622-623 consists of wire loops that oppose each other to restrain motion. FIG. 6C illustrates an embodiment in which the motion reduction elements 622-623 consist of fabric that physically restrains motion. In each of these embodiments, a flexible coupling module 621 connects the interconnected modules 610-611. As discussed above in reference to FIG. 4A, the motion reduction elements 622-623 provide sufficient intermodule motion restriction to prevent fatigue and mechanical failure of the coupling module 621 during implantation and use of the device.

In alternate embodiments, motion reduction elements may be used in all axis to maximize the amount of motion reduction provided. The implantable medical device having multiple modules typically requires sufficient motion reduction to prevent undue mechanical stresses on interconnections between the modules that may not be provided by a flexible overmold connector module 621.

Figure 7A:
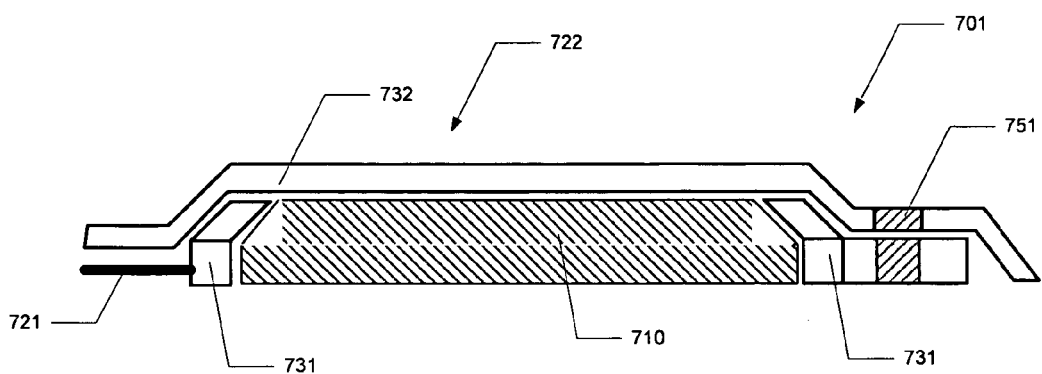
FIGS. 7A-7B are schematic diagrams illustrating the interaction of components of an overmold according to the present invention.
Figure 7B:
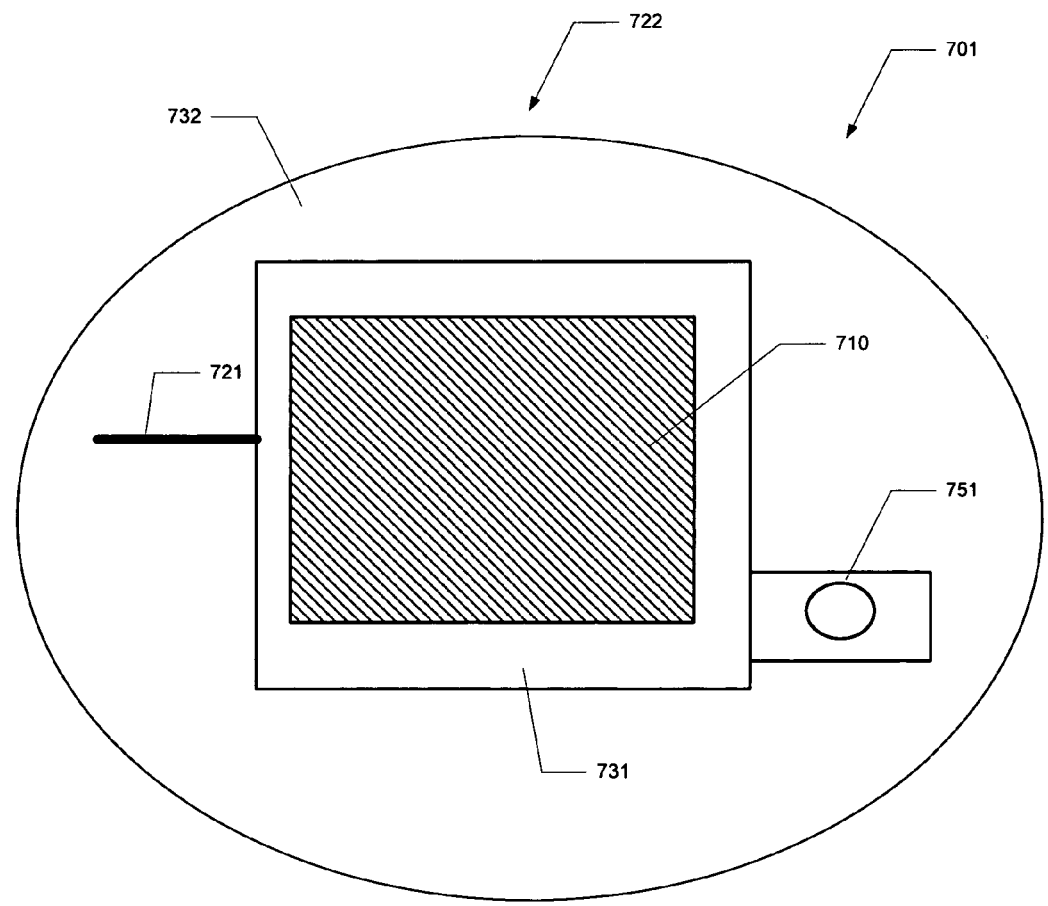

FIGS. 7A-7B are schematic diagrams illustrating the interaction of components of an implantable medical device that are part of an overmold according to the present invention. FIG. 7A provides a side view of overmold 722, including an elastomeric component 732 and non-elastomeric component 731, as it interfaces with a module 710. Non-elastomeric component 731 is typically shaped to mate with the module 710 to provide containment within the elastomeric component 732. Non-elastomeric component 731 is mechanically connected to other modules, e.g., non-elastomeric components that surround other modules, using a motion reduction element 721. Elastomeric component 732 covers all of these components in this embodiment. A through hole 751 may be located through the both elastomeric component 732 and non-elastomeric component 731 to provide an attachment point for the device 701. In some embodiments, the implantable medical device 701 may be secured in place using bone screws or similar attachment elements that secure the device 701 to the patient. Such through holes permit the device to be mechanically attached to the patient once the device 701 is positioned at a desired location.

FIG. 7B illustrates a top view of the device 701 having the elastomeric component 732 that covers the non-elastomeric component 731 surrounding the module 710. The through hole 751 used as an attachment point is shown as part of the non-elastomeric component 731 that is covered by the elastomeric component 732. The shape of the non-elastomeric component 731 and module 710 are shown as being rectangular in this embodiment. Once again, the non-elastomeric component 731 is mechanically connected to other modules using a motion reduction element 721. One skilled in the art will recognize that any shape for the non-elastomeric component 731 and module 710 may be used without deviating from the spirit and scope of the present invention, and the overall shape of the non-elastomeric component 731 need not match the shape of the module 710 to contain the module 710 within elastomeric component 732. While the overmold 722 described above may be constructed from two different materials, a soft elastomeric component and a hard non-elastomeric component, one skilled in the art may recognize a single integrated component made of either of the classes of material that contains both a surface smoothing element and a structural module restraint element may also be used without deviating from the spirit and scope of the present invention.

In addition, the elastomeric component 732 is shown as completely encapsulating the modules and components within FIG. 7. However, this elastomeric component 732 may also merely surround the module 710 but not cover the top of the module that is surrounded by the non-elastomeric component 731. Such an arrangement may render the profile of the overall device smaller. In such an alternate embodiment, a surface across the overmold connector module, integration component and the control module 710 is desired to minimize transition discontinuities that may interact with a patient after implantation.

A coupling module (not shown) passes around and through many of the elements of the overmold connector module. This coupling module is typically not restrained within the overmold as the coupling module may be expected to flex during implantation and use. The coupling module may be routed within a channel (not shown) within the overmold to ensure proper routing within the device so long as the coupling module is permitted to move sufficiently as discussed herein.

Additional details regarding overmold 722 are described in co-pending and commonly assigned U.S. patent application Ser. No. 10/730,873, entitled "OVERMOLD MODULE FOR A MODULAR IMPLANTABLE MEDICAL DEVICE."

FIG. 8A is a schematic diagram illustrating multiple modules connected by a motion reduction element within a modular medical device according to the present invention. In this embodiment, two modules 810-811 are shown being contained by respective non-elastomeric components, 831 and 832 that are part of an overmold 822 as discussed above. One of the modules 811 is located adjacent to a through-hole 851 for attaching the device 801 during implantation. A second of the two modules 810 is located adjacent to a lead connection element 813 for connecting an external lead 843 to electronics within the second module 810.

Additional details regarding the external lead connection to a device is described in co-pending and commonly assigned U.S. patent application Ser. No. 10/730,878, entitled "LEAD INTERCONNECT MODULE OF A MODULAR IMPLANTABLE MEDICAL DEVICE."

The non-elastomeric components 831, 832 are mechanically coupled together by a motion reduction element 826 that provides structural support for the device 801. Elastomeric component 833 is typically a soft and flexible element that provides a biocompatible interface between the modules and elements within the device 801 and a patient. Elastomeric component 833 typically does not provide sufficient structural support to limit the intermodule motion of modules 810-811 when the device 801 is implanted and in use. As such, the motion reduction element 826 connects the non-elastomeric components 831, 832 that are use to restrain the modules 810-811 within the device, to provide reduction of relative motion between the modules.

One skilled in the art will recognize that other embodiments for motion reduction element 826 may couple the motion reduction element 826 directly to modules 810-811. In these embodiments, motion restriction element 826 provides the same functionality by providing a support member between the modules 810-811 to reduce intermodule motion in one or more axis of motion. The choice of coupling the motion restriction element 826 to a non-elastomeric components 831-832 or coupling the motion restriction element directly to modules 810-811 may depend upon the materials used for module housings, the motion restriction element 826, elastomeric component 833 and non-elastomeric components 831, 832. In some embodiments of the modules 810-811, electronics within the modules may be damaged during fabrication of the elastomeric component 833 due to the temperatures and related environmental conditions present when the elastomeric component 833 is made. The non-elastomeric components 831-832 may be used to create structures to contain the modules 810-811 within a constructed elastomeric component 833 after the elastomeric component 833 is completed. As such, electronics within the modules 810-811 may not need to encounter the undesirable fabrication conditions.

The intermodular motion within the device 801 may be limited in order to prevent mechanical failures of coupling module 851 that are used to interconnect components within the modules 810-811 in order to construct a working implantable medical device. Coupling module 851 may require motion during implantation and use to prevent failures of the connections therein. As such, the coupling module 851 may not provide sufficient intermodule motion reduction to meet the structural support of the device. The motion reduction elements 826 provide this additional structural support.

In the embodiment shown in FIG. 8A, the coupling module 851 provides a connection between module 810 and module 811. The coupling module 851 need not be connected to these modules 810-811 on adjacent sides of the modules 810-811 as the flexible coupling module 851 may possess multiple non-linear bends to route the coupling module 851 between any two desired locations on the modules 810-811. These multiple non-linear bends and the relative length of coupling module 851 may contribute to its flexibility in one or more directions. However, the route taken by the coupling module 851 may contribute to the amount of mechanical stress encountered by the coupling module 851 during implantation and use; therefore, the route taken by the coupling module 851 may also contribute to the motion reduction requirements for motion restriction element 826.

Additional details regarding coupling modules are provided in co-pending and commonly assigned U.S. patent application Ser. No. 10/731,699, entitled "COUPLING MODULE FOR A MODULAR IMPLANTABLE MEDICAL DEVICE."

Because the device 801 may need to be shaped to a custom orientation during implantation in order for the device 801 to effectively mate with a patient at the implantation location, the shape of the motion reduction element 826 may be modified into a desired, but rigid orientation at the time of implantation. As discussed above, the motion reduction element 826 may be constructed using wires, fabric, and other materials. Preferably, the materials used to fabricate the motion reduction element 826 may be bent or otherwise shaped to modify the shape of a device.

Figure 8B:
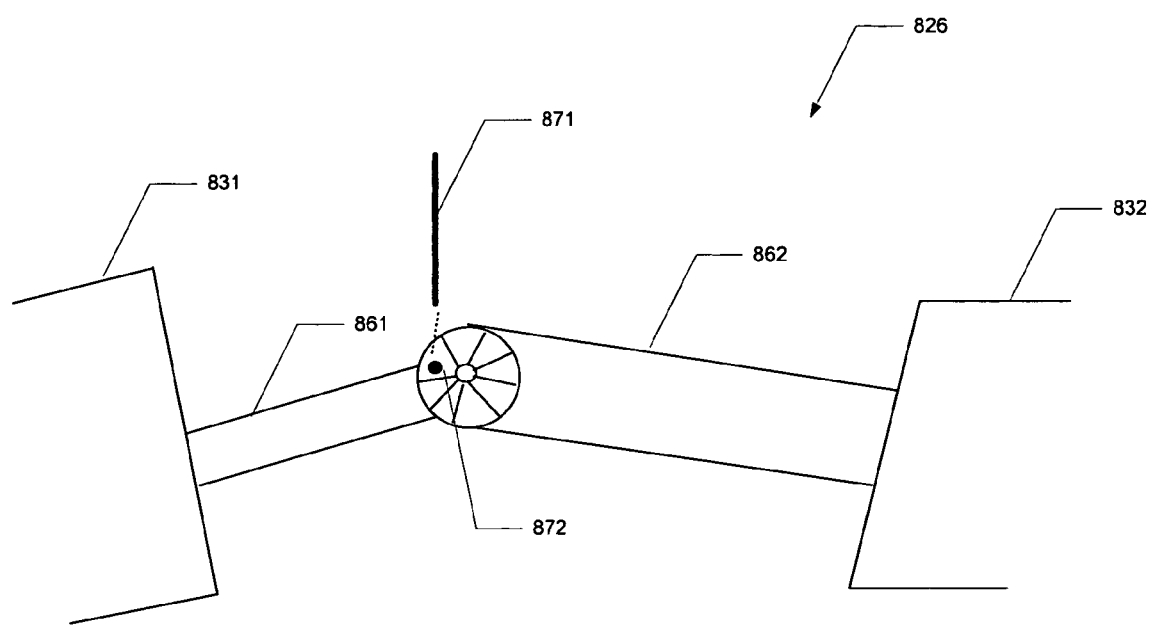

FIG. 8B illustrates an embodiment in which one or more rigid materials, such as non-elastomeric materials used to form non-elastomeric components 831, 832, may be used to construct support members 861-862. In this embodiment, a mechanical moving element 872 may be required to provide an ability to shape the motion reduction element 826. The mechanical moving element 872 may include a ball and socket arrangement, a rod and slot arrangement, a geared hinge arrangement, and many other motion reduction mechanisms. In these embodiments, these mechanical moving element 872 may utilize a locking mechanism 871 such as lock pins, adhesives and related locking mechanisms to secure the motion reduction element 826 into a desired orientation once set by a physician.

During implantation of a device 801, the physician may manipulate the shape and orientation of the device by manipulating the settings the mechanical moving element 872 to alter the relative position of support members 861-862. Once the device is placed into a desired orientation, locking mechanism 871, such as a pin, may be inserted into the mechanical moving element 872 to retain the desired orientation of the device 801. Adhesives, cements and other materials may also be utilized to restrain the locking mechanism and mechanical orientation element 872 as needed.

Figure 9A:
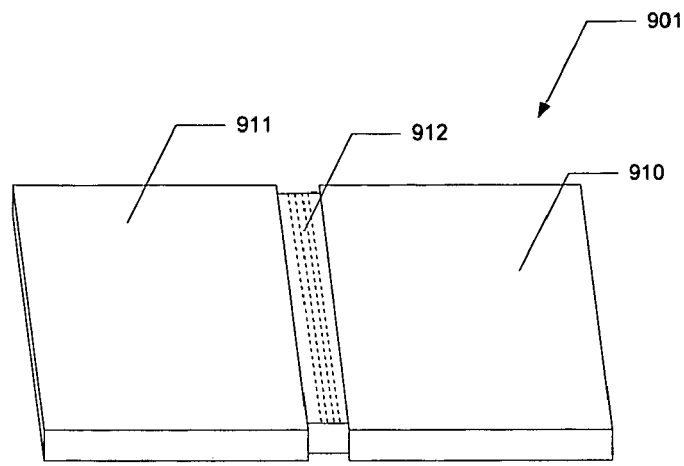
FIGS. 9A-9F are schematic diagrams illustrating various embodiments of coupling modules for use in connecting multiple modules within a modular implantable medical device according to the present invention.
Figure 9B:
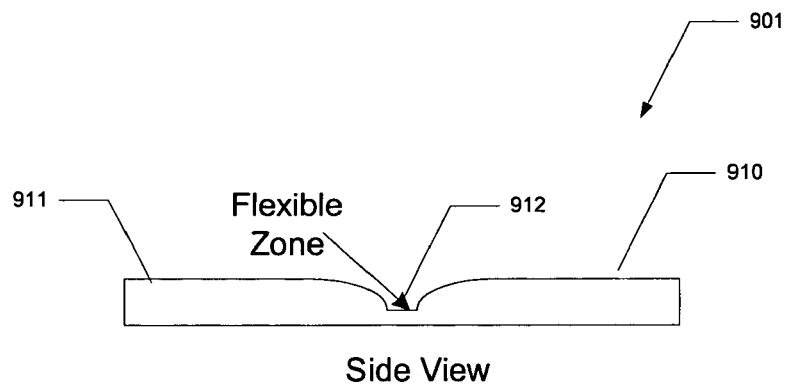
Figure 9C:
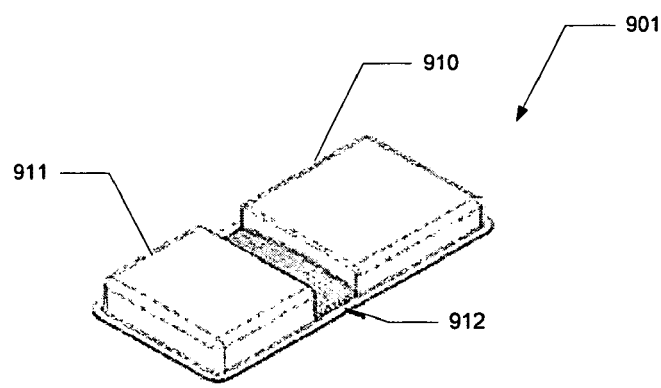

FIGS. 9A-9F are schematic diagrams illustrating various embodiments of coupling modules for use in connecting multiple modules within a modular implantable medical device according to the present invention. FIGS. 9A-9C are schematic diagrams illustrating two distributed modules having a coupling module with a single degree of motion according to an embodiment of the present invention. The implantable medical device 901 shown in this embodiment is constructed from two individual modules 910-911 that are physically linked using a flexible coupling module 912 that may be referred to as a coupling module. This coupling module 912 possesses a coupling body having a connection end at each connection interface with a module. In each of the three embodiments shown in FIGS. 9A-9C, a flexible zone 912 exists between the two modules 910-911. In FIG. 9A, the zone 912 is narrower than the common dimension of the modules 910-911 as it is constructed as a separate physical element. In contrast, the zone 912 in both FIGS. 9B-9C are an integral part of the combined structure. FIG. 9B illustrates the zone 912 to be a narrow connection zone between two compartments of a common structure in which each module is located within the two compartments 910-911. FIG. 9C shows the zone 912 to be a distinctly separate ribbed element that separates the two modules 910-911.

In all cases, the power coupling module 912 provides a structure that is flexible in a single axis of rotation. The axis of rotation is parallel to the two modules and allows the coupling module to be flexible between is narrowest dimension. As such, the two modules 910-911 may be rotated to create a convex surface for the entire structure 901. The coupling module 912 may be semi-rigid to permit the structure 901 to be manipulated into a desired shape and then retain a desired orientation. Alternatively, the coupling module 912 may be flexible to permit the two modules 910-911 to move about its axis of rotation as needed.

Within the coupling module 912, a void or passageway exists between the two module 910-911 that permits components and elements within the modules in one module 910 to be coupled to other components and elements in the other module 911. The coupling module 912 provides a structural support element that protects these connections between modules from damage. The coupling module 912 may also contain hermetic and non-hermetic interfaces between a module and the coupling module 912 to environmentally protect the modules. These hermetic and non-hermetic interfaces refer to the interfaces between the modules and the coupling modules; the nature of these interfaces may be independent from and hermetic interface characteristics of the overall device 901 and a patient. The motion reduction elements described herein provide necessary structural support to reduce intermodule motion while permitting the coupling modules 912 to remain flexible in at least a single axis of motion. The motion reduction elements attempt to reduce the intermodule motion to within a range of motion that is within a permissible range of motion for the coupling modules to minimize structural damage and fatigue as the coupling module 912 flexes while the medical device 910 is implanted and used.

Figure 9D:
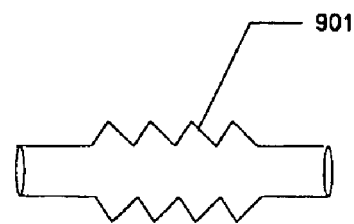

FIG. 9D illustrates a coupling module 901 that possesses a set of bellows to assist in the flexing of the coupling module during implantation and use. This embodiment of the coupling illustrates a coupling module constructed from a coupling body having convolutions in which variations in the diameter of the coupling body exist along a length of the coupling body to assist in providing motion in one or more axis of motion. Coupling bodies having corrugations, convolutions, bellows and similar variations in diameter are coupling body shapes within the spirit and scope of the present inventions are recited within the attached claims.

Figure 9E:
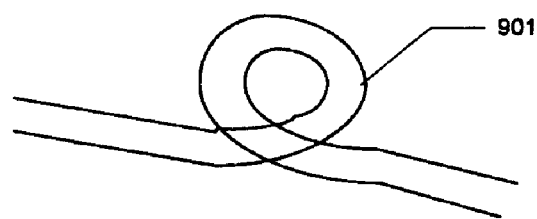
Figure 9F:
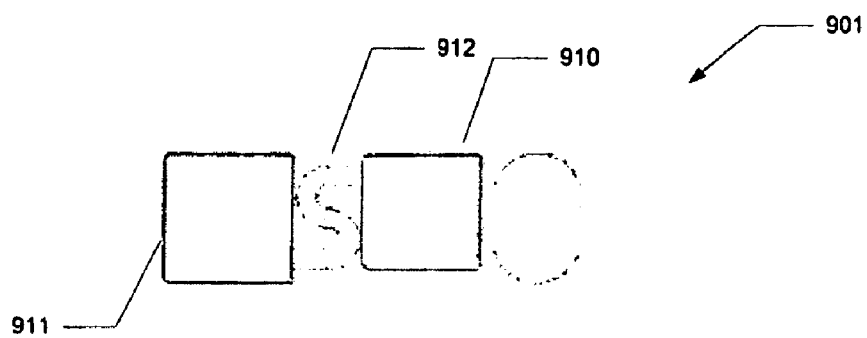

FIG. 9E illustrates that a coupling module 901 may be arranged to include a helix-like structure to prove an arrangement that supports motion of the separate modules relative to each other while not requiring significant rotation of the coupling module 901 to support the motion. An embodiments in FIG. 9F include an arrangement and shape for a connection body used to construct a coupling module possessing at least one non-linear bend along its length between its connection ends. As discussed above with reference to FIG. 8B, all of these coupling module embodiments may be used to connect any two points on any two modules within a device as long as the coupling module may be routed between the two points.

One skilled in that are will recognize that from the above configurations, any arrangement for a coupling module 901 may be possible to connect two modules 910-911 without deviating from the spirit and scope of the present invention as recited within the attached claims. Any such arrangement for a coupling module 901 merely needs to provide needed flexibility for expected motion between interconnected modules while providing sufficient structural support and protection for the interconnections during implantation and use.

Figure 10:
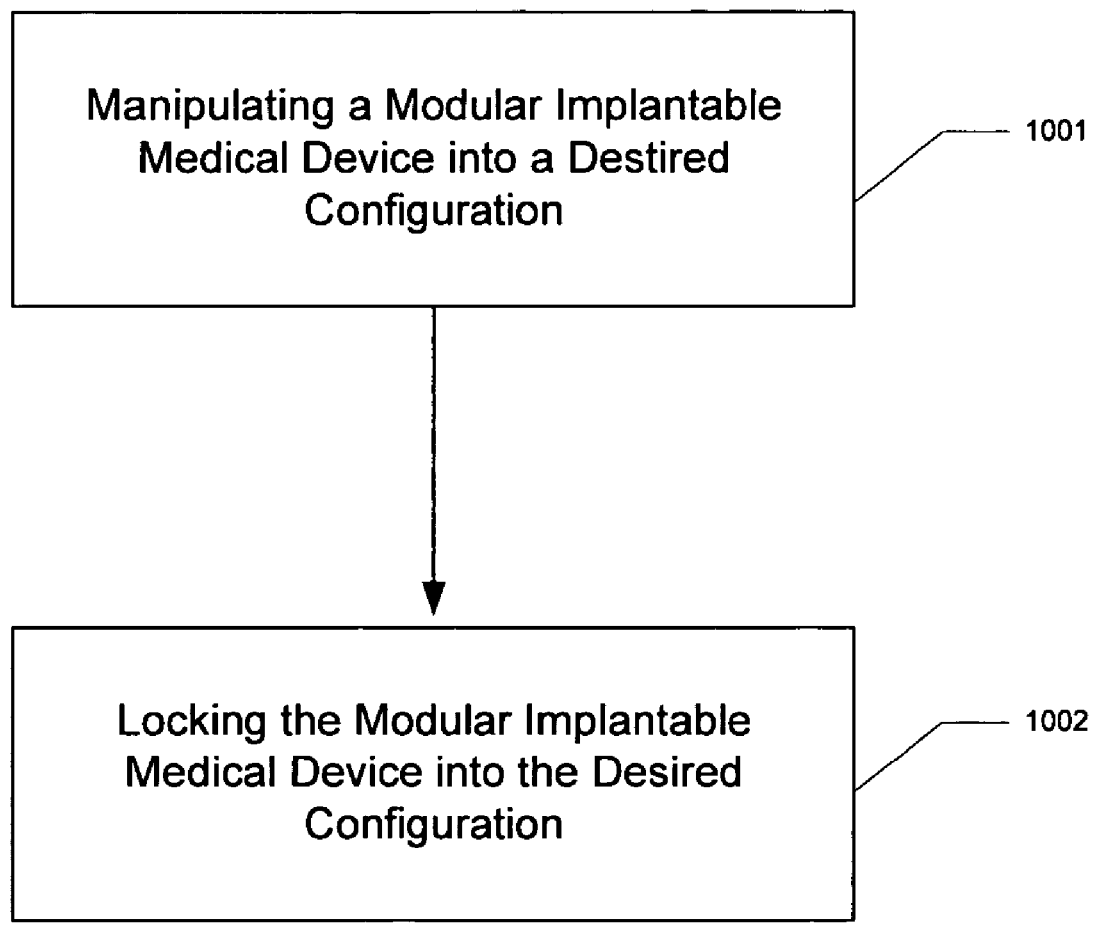
FIG. 10 is a flowchart illustrating a method for shaping a modular implantable medical device according to the present invention.

FIG. 10 is a flowchart illustrating a method for shaping a modular implantable medical device according to the present invention. Typically, an implantable medical device according to the present invention is constructed into a shape and orientation expected to provide a reduced profile by attempting to mate the shape of the device 201 to a patient's body implantation location. At the time of implantation, the implantable medical device 201 may be manipulated (1001) in order to better mate the shape and orientation of the device 201 to the patient. As discussed above, the device may be manipulated with motion reduction elements 826 modifying its shape to provide structural support for modules 210-212 within the device 201. The shape and orientation may be manipulated into a desired position by changing the shape of the motion reduction device 826.

Once a desired shape and orientation of the device 201 has been obtained, the implantable medical device 201 may be locked into its desired orientation (1002) by locking a locking mechanism 872 on the motion reduction element 826. As discussed above, the motion reduction elements 826 provide structural support to the modules 210-212, and thus define an orientation for the device 201, by reducing intermodule motion within the device. The locking mechanism ensures that the motion reduction elements 826 remains in a desired orientation. To complete the process, a separate securing element, such as cement or adhesive may be inserted into the motion reduction elements 826 to prevent any further movement of the motion reduction elements 826 and thereby ensure that the desired orientation of the device is maintained.

While the above embodiments of the present invention describe reducing relative intermodular motion within a modular implantable medical device, one skilled in the art will recognize that the use of a module structure are merely example embodiments of the present invention. It is to be understood that other embodiments may be utilized and operational changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a module for reducing intermodular motion within a modular implantable medical device.

The invention claimed is:

1. An implantable medical device comprising:
   a plurality of interconnected modules, each of the modules comprising a respective housing to house each respective module;
   an overmold comprising a first substantially flexible component that at least partially encapsulates each of the housings, and second and third components that are located adjacent to at least one side surface of a respective one of the housings, wherein the first component comprises an elastomeric material and the second and third components comprises a non-elastomeric material; and
   a motion reduction element within the overmold to reduce relative motion between at least two of the modules,
   wherein the motion reduction element, couples the second and third components of the overmold.

2. The implantable medical device of claim 1, wherein the motion reduction element is located between two of the modules.

3. The implantable medical device of claim 1, wherein at least one of the second and third components comprises the motion reduction element.

4. The implantable medical device of claim 1, wherein the motion reduction element comprises a wire-like element.

5. The implantable medical device of claim 1, wherein the motion reduction element comprises a fabric.

6. The implantable medical device of claim 1, wherein the motion reduction element comprises at least one of a cement, a polymer, and a shape memory alloy.

7. The implantable medical device of claim 1, wherein the motion reduction element comprises a fiber.

8. The implantable medical device of claim 1, wherein the motion reduction element comprises at least two rigid members coupled together with a mechanical moving element.

9. The implantable medical device of claim 8, wherein the mechanical moving element is a ball and socket element.

10. The implantable medical device of claim 8, wherein the mechanical moving element is a rod and slot element.

11. The implantable medical device of claim 8, wherein the mechanical moving element is a geared hinge element.

12. The implantable medical device of claim 1, wherein the implantable medical device comprises an implantable neurostimulator.

13. The implantable medical device of claim 1, wherein the housing of at least one of the modules is hermetic.

14. The implantable medical device of claim 1, wherein a respective housing of at least one of the modules comprises a rigid material.

15. The implantable medical device of claim 14, wherein the rigid material comprises at least one of titanium, stainless steel or ceramic.

16. An implantable medical device comprising:
    a plurality of interconnected modules, each of the modules comprising a respective housing to house each respective module;
    an overmold that at least partially encapsulates each of the housings; and
    a motion reduction element within the overmold to reduce relative motion between at least two of the modules,
    wherein the overmold comprises a first substantially flexible component that at least partially encapsulates each of the housings, and second and third components that are located adjacent to side surfaces of respective ones of the housings, and
    wherein the motion reduction element couples the second and third components of the overmold and comprises a first motion reduction element that protrudes from the second component of the overmold, the implantable medical device further comprising a second motion reduction element that protrudes from the third component of the overmold, wherein first and second motion reduction elements interact to reduce relative motion between modules associated with the second and third components.

17. An implantable medical device comprising:
    a plurality of interconnected modules, each of the modules comprising a housing;
    an overmold that at least partially encapsulates each of the housings; and
    a motion reduction element within the overmold to reduce relative motion between at least two of the modules,
    wherein the motion reduction element comprises at least two rigid members coupled together with a mechanical moving element, and
    wherein the mechanical moving element includes a locking element to permit the at least two rigid members to be positioned into a desired location and to permit the locking element to retain the mechanical moving elements in the desired position.

18. The implantable medical device of claim 17, wherein the locking element is an insertable pin element.

19. The implantable medical device of claim 17, wherein the locking element is an adhesive element.

20. An implantable medical device comprising:
    a plurality of interconnected modules, each of the modules comprising a respective housing to house each respective module;
    an overmold comprising a first substantially flexible component that at least partially encapsulates each of the housings, and second and third components that are located adjacent to at least one side surface of a respective one of the housings, wherein the first component comprises an elastomeric material and the second and third components comprise a non-elastomeric material; and
    means within the overmold for reducing relative motion between, at least two of the modules,
    wherein the means within the overmold for reducing relative motion between at least two of the modules couples the second and third components of the overmold.

21. The implantable medical device of claim 20, wherein the means for reducing relative motion is located within the overmold between two of the modules.

22. The implantable medical device of 20, wherein at least one of the second and third components comprises the means for reducing relative motion between modules.

23. The implantable medical device of claim 20, wherein the implantable medical device comprises an implantable neurosrimulator.

24. An implantable medical device comprising:
    a plurality of interconnected modules, each of the modules comprising a housing;
    an overmold that at least partially encapsulates each of the housings; and
    means within the overmold for reducing relative motion between at least two of the modules, wherein the means for reducing relative motion comprises:
    means for permitting motion between at least two of the modules to a configuration; and
    means for locking the modules in the configuration.

25. An implantable medical device comprising:
- a plurality of interconnected modules, each of the modules comprising a respective housing to house each respective module;
- an overmold that at least partially encapsulates each of the housings;
- a coupling module to couple at least two of the modules, wherein the coupling module is flexible to allow at least one degree of relative motion between the modules, the at least one degree of relative motion comprising rotational motion; and
- a motion reduction element within the overmold to reduce relative motion between the at least two of the modules in the at least one degree.

26. The implantable medical device of claim 25, wherein the coupling module is hermetic.

27. An implantable medical device comprising:
- a plurality of interconnected modules, each of the modules comprising a respective housing to house each respective module;
- an overmold that at least partially encapsulates each of the housings, the overmold comprising a first component comprising an elastomeric material, and second and third components comprising nonelastomeric material; and
- a motion reduction element within the overmold to reduce relative motion between at least two of the modules, wherein the motion reduction element couples the second and third components of the overmold.

* * * * *

UNITED STATES PATENT AND TRADEMARK OFFICE
CERTIFICATE OF CORRECTION

| | |
|---|---|
| PATENT NO. | : 7,392,089 B2 |
| APPLICATION NO. | : 10/731881 |
| DATED | : June 24, 2008 |
| INVENTOR(S) | : Wahlstrand et al. |

Page 1 of 1

It is certified that error appears in the above-identified patent and that said Letters Patent is hereby corrected as shown below:

Col. 15, Line 6: "flexible component" should read --flexible, elastomeric component--

Col. 15, Line 8: "third components" should read --third non-elastomeric components--

Col. 15, Line 10: "housings, wherein the first component comprises an elastomeric material and the second and third components comprises a non-elastomeric material; and" should read --housings; and--

Col. 16, Line 33: "flexible component" should read --flexible, elastomeric component--

Col. 16, Line 35: "third components" should read --third non-elastomeric components--

Col. 16, Line 37: "housings, wherein the first component comprises an elastomeric material and the second and third components comprises a non-elastomeric material; and" should read --housings; and--

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,392,089 B2 | |
| APPLICATION NO. | : 10/731881 | |
| DATED | : June 24, 2008 | |
| INVENTOR(S) | : Carl D. Wahlstrand et al. | |

It is certified that error appears in the above-identified patent and that said Letters Patent is hereby corrected as shown below:

This certificate supersedes the Certificate of Correction issued June 22, 2010. The certificate is vacated since errors in the Certificate of Correction were requested in error. The claims as printed in patent are correct.

Signed and Sealed this
First Day of February, 2011

David J. Kappos
*Director of the United States Patent and Trademark Office*